United States Patent

Kottenhahn et al.

[11] Patent Number: 5,859,248
[45] Date of Patent: Jan. 12, 1999

[54] PROCESS FOR THE PRODUCTION OF A β-AMINO ALCOHOL

[75] Inventors: Matthias Kottenhahn; Karlheinz Drauz, both of Freigericht, Germany; Hans Hilpert, Reinach, Switzerland

[73] Assignees: F. Hoffman-La Roche AG, Basel, Switzerland; Degussa Aktiengesellschaft, Frankfurt, Germany

[21] Appl. No.: 793,711

[22] PCT Filed: Aug. 17, 1995

[86] PCT No.: PCT/EP95/03280

§ 371 Date: Mar. 3, 1997

§ 102(e) Date: Mar. 3, 1997

[87] PCT Pub. No.: WO96/07642

PCT Pub. Date: Mar. 14, 1996

[30] Foreign Application Priority Data

Sep. 3, 1994 [DE] Germany .......................... 44 31 530.9

[51] Int. Cl.[6] .................................................. C07D 217/22
[52] U.S. Cl. ............................................................ 546/146
[58] Field of Search ............................ 546/146; 548/229, 548/232, 473, 406; 560/39

[56] References Cited

U.S. PATENT DOCUMENTS 5,455,353  10/1995  Hilpert .................................... 546/146

OTHER PUBLICATIONS

Morrison and Boyd: Organic Chemistry 3rd Edition. see pp. 587 and 673. Jan., 1975.

CA Abstract No. 90:168996 (Abstract of DE 2725732 Published in 1978 (see pp. 9–12 of CAS Search Report).

*Primary Examiner*—Alan L. Rotman
*Assistant Examiner*—Charanjit S. Aulakh
*Attorney, Agent, or Firm*—Cushman Darby&Cushman IP Group of Pillsbury Madison & Sutro LLP

[57] ABSTRACT

A process for producing 2-[3(S)-amino-2-(R)-hydroxyl-4-phenyl butyl]-N-tert,butyl decahydro-(4aS,8aS)-isoquinoline-e(S)-carboxamide of the formula (I) via 3(S)-[lower alkoxy carbonyl amino, phenoxy carbonyl amino or benzyl oxycarbonyl amino]-2-hydroxy-4-phenyl butyric acid and process for producing said acid.

1 Claim, No Drawings

PROCESS FOR THE PRODUCTION OF A β-AMINO ALCOHOL

This application is a 371 of PCT/EP95/03280, filed on Aug. 17, 1995, which is now published as WO/96/07642 on Mar. 14, 1996.

The present invention relates to a novel process for the production of a β-amino alcohol, namely 2-[3-(S)-amino-2(R)-hydroxy-4-phenylbutyl]-N-tert.-butyl-decahydro-(4aS, 8aS)-isoquinoline-3(S)-carboxamide of the formula

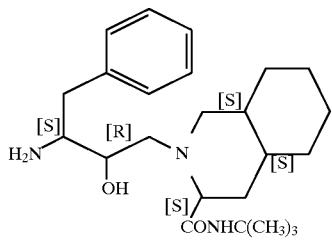

The compound of the above formula I is specifically described, for example, in Example 1 of European published patent 0 432 695 and is a valuable intermediate for the production of pharmacologically active compounds. The compound of the formula I may thus, as described in Examples 1 and 3 of the stated published European patent, be converted into pharmacologically active substances which are suitable for the treatment of viral infections, in particular those infections caused by HIV and other retroviruses.

The process according to the invention is characterised in that a) L-phenylalanine of the formula

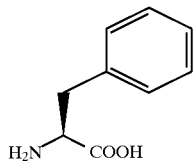

is reacted with phthalic anhydride, b) the resultant 3-phenyl-2(S)-phthalimidopropionic acid of the formula

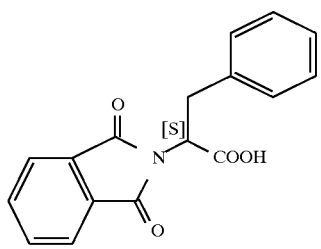

is converted into the corresponding acid chloride, c) the resultant 3-phenyl-2(S)-phthalimidopropionic acid chloride of the formula

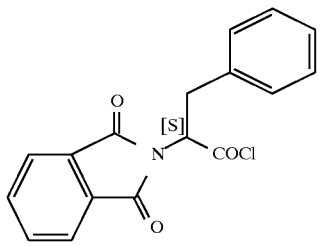

is reduced, d) the resultant 3-phenyl-2(S)-phthalimidopropan-1-al of the formula

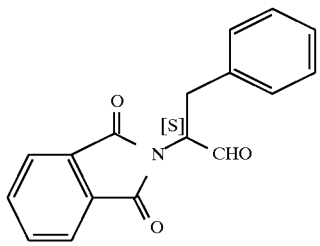

is transformed into the 1-cyano-3-phenyl-2(S)-phthalimidopropan-1-ol of the formula

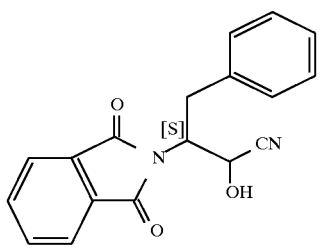

e) the resultant nitrile of the formula VI is hydrolysed, f) the 3(S)-amino-2-hydroxy-4-phenylbutyric acid formed of the formula

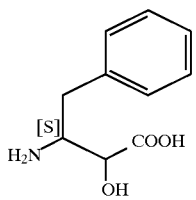

is reacted with a low alkyl ester or the phenyl or benzyl ester of chloroformic acid, g) a resultant 3(S)-[low alkoxycarbonylamino-, phenyloxycarbonylamino- or benzyloxycarbonxylamino]-2-hydroxy-4-phenylbutyric acid of the general formula

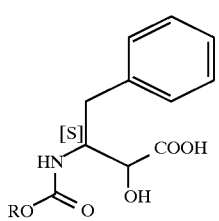

in which R means low alkyl, phenyl or benzyl, is cyclised, h) the resultant (4S,5S)-4-benzyl-2-oxo-oxazolidine-5-carboxylic acid of the formula

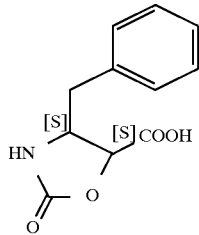

IX is esterified with a low alkanol, i) the resultant (4S,5S)-4-benzyl-2-oxo-oxazolidine-5-carboxylic acid low alkyl ester of the general formula

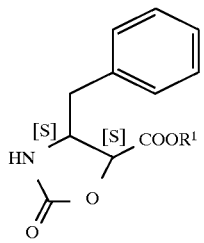

X in which $R^1$ means low alkyl, is reduced j) the resultant (4S,5S)-4-benzyl-5-hydroxymethyl-oxazolidin-2-one of the formula

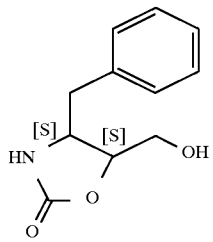

XI is reacted in the presence of a base with a sulphonic acid chloride of the general formula

$R^2$—SO$_2$Cl in which $R^2$ means low alkyl, phenyl or phenyl mono- or disubstituted by halogen, low alkyl or nitro, k) a resultant sulphonic acid ester of the general formula

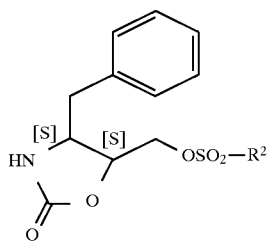

XII in which $R^2$ has the above-stated meaning, is reacted in the presence of a base with N-tert.-butyl-decahydro-(4aS,8aS)-isoquinoline-3(S)-carboxamide of the formula

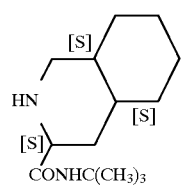

XIII and l) the resultant 2-[(4S,5R)-4-benzyl-2-oxo-oxazolidin-5-yl methyl]-N-tert.-butyl-decahydro-(4aS,8aS)-isoquinoline-3(S)-carboxamide of the formula

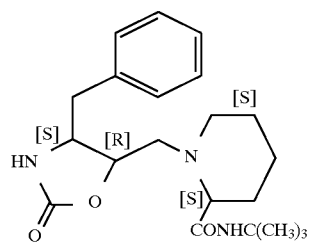

XIV is treated with a base.

The 3-phenyl-2(S)-phthalimidopropan-1-al of the formula V is conveniently obtained by heating L-phenylalanine of the formula II with phthalic anhydride in toluene, reacting the resultant N-protected L-phenylalanine of the formula III with oxalyl chloride in toluene and catalytic quantities of dimethylformamide and catalytically (Pd/C) hydrogenating the resultant acid chloride of the formula IV, which corresponds to the desired aldehyde of the formula V, in the presence of an HCl scavenger, such as 1,2-butylene oxide in toluene.

In order to produce the nitrile VI, a solution of the aldehyde V, for example in toluene, is advantageously combined with aqueous sodium pyrosulphite and the resultant addition product of pyrosulphite and the aldehyde V, optionally in a solvent, such as water or optionally aqueous methylene chloride or toluene, is treated with sodium cyanide. In one variant, a mixture of the aldehyde V and zinc(II) bromide is also preferably reacted in a solvent, such as methylene chloride, at −70° to 0° C., for example at −15° C., with trimethylsilyl cyanide and the resultant silyl ether cyanohydrin is cleaved by adding a solution of citric acid in ethanol.

In another variant, a solution of the aldehyde V, for example in toluene, is reacted with an aqueous NaCN solution with the addition of acid, so maintaining a pH value of between 5 and 7.5, to yield the cyanohydrin.

In another variant, a solution of the aldehyde V and of benzyl chloroformate in methylene chloride is advantageously combined in the presence of benzyl-triethylammonium chloride with cooling, conveniently at −10° to 0° C., with sodium cyanide and the resultant benzyl carbonate of the cyanohydrin is hydrogenated in a solvent, such as ethanol or methylene chloride, wherein the nitrile VI is obtained.

The nitrile VI is advantageously hydrolysed by means of mineral acids in the presence of a cosolvent, such as for example 1,4-dioxane. Hydrolysis is preferably performed with hydrochloric acid at a temperature of between approximately 70° C. and reflux temperature. It was found in the context of the present invention that the absence of 1,4-dioxane results in significant acceleration of the reaction. Complete conversion is achieved after 10 to 20 hours. By increasing the temperature to >125° C. (which entails the use of pressurised apparatus) it is possible to shorten the hydrolysis time considerably. The phthalic acid formed is separated by cooling the reaction mixture to 20° to −15° C., preferably to 0°–5° C., filtering it, wherein almost the entirety of the phthalic acid is present in the crystallisate. The filtrate contains virtually pure β-amino acid VII, which is used in the next stage, preferably without being isolated.

Carbamoylation of the β-amino acid VII is performed, for example, by combining the filtrate from the preceding stage at pH 5–12, preferably 8–10, and at −15° to 50° C., preferably at 0°–10° C., with a chloroformic acid low alkyl or benzyl ester. The solution contains virtually pure acid VIII, which is used in the next stage, preferably without being isolated. Isolation may optionally be achieved by adjusting the pH value 1–3 with a mineral acid after completion of the reaction (approximately 1 hour) and purifying the acid VIII by extraction with ethyl acetate or hot toluene and crystallisation from toluene.

Oxazolidinone ring closure to yield the acid IX is conveniently performed by combining an aqueous suspension of the acid VIII at room temperature with sodium hydroxide solution. In order to isolate the acid IX, the reaction mixture may be extracted with a suitable organic solvent, such as ethyl acetate and the like, and the residue then crystallised. The acid IX is conveniently isolated by direct crystallisation from the reaction mixture by adjusting the pH value to −1 to +1 and seeding the mixture.

Esterification of the acid IX is conveniently performed in the presence of a catalytic quantity of an acid, such as sulphuric acid, with heating, for example to reflux temperature.

Reduction of the 2-oxo-oxazolidine-5-carboxylic acid ester X is conveniently performed in a solvent, such as toluene, tetrahydrofuran or a low alkanol, preferably methanol or ethanol, at a temperature of between 0° and 60° C., preferably at 0°–25° C., by means of sodium bis(2-methoxyethoxy)aluminium hydride, lithiumaluminium hydride or preferably sodium borohydride.

The acid IX is conveniently converted into the alcohol XI without the ester X being isolated.

In one variant, the acid IX is produced by
a) converting the 1-cyano-3-phenyl-2(S)-phthalimido-propan-1-ol of the formula

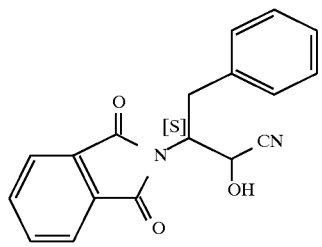

VI in the presence of a low alkanol with a strong acid into a salt of the imino ether of the formula

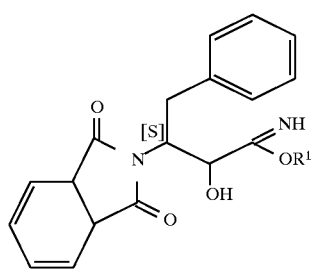

VI' in which R$^1$ is low alkyl, b) the salt of the imino ether of the formula VI' is hydrolysed, c) the resultant α-hydroxy acid ester of the formula

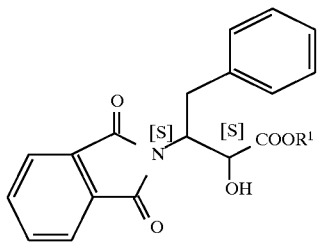

XV is converted first with a base and then a strong acid into the α-hydroxy-β-amino acid ester of the formula

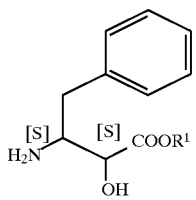

XVI in which R$^1$ is low alkyl, d) the α-hydroxy-β-amino acid ester of the formula XVI is reacted with a low alkyl ester or the phenyl or benzyl ester of chloroformic acid, e) a resultant 3(S)-[low alkoxycarbonylamino-, phenoxycarbonylamino- or benzyloxycarbonylamino]-2(S)-hydroxy-4-phenylbutyric acid low alkyl ester of the formula

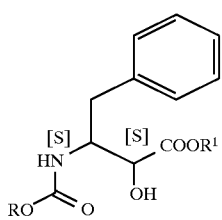

XVII in which R$^1$ is low alkyl and R is low alkyl, phenyl or benzyl, is cyclised.

By reacting the cyanohydrin VI in the presence of a low alkanol R$^1$—OH with a strong acid, such as HCl, in a solvent, such as a low alkanol R$^1$—OH, CH$_2$Cl$_2$, toluene, t.-butyl methyl ether or preferably a mixture of CH$_2$Cl$_2$ and R$^1$—OH or of toluene and R$^1$—OH, with cooling to −10° to +10° C., conveniently to 0° C., the corresponding salt of the imino ether of the formula VI' is obtained.

This is hydrolysed, for example, with aqueous ethyl acetate, with CH$_2$Cl$_2$ or preferably with aqueous toluene and R$^1$—OH to yield the hydroxy acid ester XV.

The compound of the formula XVI is obtained by treating a compound XV first with a base, such as methylamine, and then with a strong acid, such as HCl, in a solvent, such as THF or preferably an alcohol, such as R$^1$—OH, in particular methanol, at a temperature of −10° to +20° C., preferably at 0° C. for the first stage and at 20° C. for the second stage.

A solution of the α-hydroxy-β-amino acid ester XVI or preferably a salt thereof, such as the acetate or hydrochloride, in water or toluene is converted at −10° to +10° C., preferably at 0° C., in the presence of a base such as NaOH, with a low alkyl ester or the phenyl or benzyl ester of chloroformic acid, into the corresponding N-carboxylated compound of the formula XVII.

Cyclisation of a compound XVII to yield the compound IX is achieved by reacting the compound in methanol, ethanol or water firstly with a base, such as NaOH, at approximately room temperature and then with sodium methylate with refluxing. It may be advantageous to add the base in portions in order to avoid epimerisation on C-2. In one variant, the compound XVII is directly reacted with the base at 30°–35° C.

The alcohol XI is sulphonated in a solvent, such as ethyl acetate or preferably acetone or tetrahydrofuran, in the presence of a base, such as triethylamine or preferably N-methylmorpholine, at a temperature of between 0° and 60° C., preferably between 20° C. and 40° C.

A sulphonic acid ester of the formula XII is conveniently reacted with the amide XIII in a solvent, such as dimethyl sulphoxide, a hydrocarbon, for example toluene, triethylamine or a low alkanol, for example ethanol, or a ketone, preferably 4-methyl-2-pentanone, in the presence of a base, such as a low alkylamine or an alkali metal carbonate, preferably triethylamine or sodium carbonate, with heating up to reflux temperature, preferably at 50°–150° C., preferably[sic] at 80°–110° C. In order to purify the resultant oxazolidinone XIV, a readily crystallised salt, such as a sulphonate, in particular p-toluene, p-bromophenyl or p-nitrophenyl sulphonate, is produced by adding a strong acid, such as sulphuric or preferably hydrochloric acid.

Once the sulphonic acid has been removed by extraction with a base, preferably sodium bicarbonate, in a solvent, preferably ethyl acetate, cleavage of the oxazolidinone XIV conveniently proceeds in a solvent, such as water, ethanol or a mixture thereof, by means of a base, such as sodium or potassium hydroxide with heating up to reflux temperature, preferably at 20°–100° C., preferably[sic] at 80° C.

The compound of the formula XIII used as the starting substance is known and corresponds to the compound of the formula VII in published European patent 0 432 695.

The term "low alkyl" used above denotes linear and branched saturated hydrocarbon residues having 1–6, preferably 1–4, carbon atoms, such as methyl, ethyl, n-propyl, isopropyl, n-butyl, isobutyl, sec.-butyl, tert.-butyl, pentyl, hexyl and the like. The term "halogen" denotes fluorine, chlorine, bromine and iodine.

The following Examples are intended to illustrate the present invention, but not to restrict it in any way. All temperatures are stated in degrees Celsius.

EXAMPLE 1
(III→IV→V)

A) A suspension of 82.6 g of L-phenylalanine and 74.1 g of phthalic anhydride in 600 ml of toluene was refluxed under argon for 8 hours. The resultant suspension was cooled to room temperature and combined with 0.5 ml of dimethylformamide, followed by 66.64 g of oxalyl chloride. After 2 hours' stirring, argon was blown into the solution.

B) The solution containing the 3-phenyl-2(S)-phthalimidoproionyl chloride was diluted with 500 ml of toluene and combined with 72.11 g of 1,2-butylene oxide. 23.5 g of palladium on carbon (5%) and 100 ml of toluene were added to the solution. The suspension was hydrogenated for 17 hours with stirring and then filtered and the residue washed with 200 ml of toluene, wherein 3-phenyl-2(S)-phthalimidopropan-1-al was obtained.

EXAMPLE 2
(V→VI)

A suspension of 5 g of 3-phenyl-2(S)-phthalimidopropan-1-al and 4.43 g of zinc bromide in 50 ml of methylene chloride was combined with stirring at −15° with a solution of 1.95 g of trimethylsilyl cyanide in 5 ml of methylene chloride and stirred for 5 hours at −15°. The resultant silyl ether was cleaved at −10° by adding a solution of 5 g of citric acid in 50 ml of ethanol. The mixture was evaporated and the residue combined with water and extracted with methylene chloride. The organic extracts were dried, filtered and the filtrate evaporated. The residue contained 5.45 g (99%) of crude 3-(1,3-dioxo-2,3-dihydro-1H-isoindol-2-yl)-2-hydroxy-4-phenylbutyronitrile as a 74:26 mixture of the (2S,3S) and (2R,3S) isomers, IR (KBr): 3437 m (OH), 2250 w (C≡N), 1775 m and 1713 s (C=O of imide).

EXAMPLE 3
(V→VI)

A solution of 95.05 g of sodium pyrosulphite in 1 l of water was added with stirring to the solution containing the 3-phenyl-2(S)-phthalimido-propan-1-al (Example 1). After 4.5 hours' stirring, the aqueous layer containing the addition product of bisulphite and the above aldehyde was washed with toluene. The toluene layers were extracted with water. 1200 ml of methylene chloride were added to the water layers and the mixture was combined with stirring at room temperature with a solution of 41.66 g of sodium cyanide in 330 ml of water. Water was added after 1.2 hours' stirring. The separated aqueous layer was extracted with methylene chloride. The organic layers were dried and filtered and the residue was washed with methylene chloride. The filtrates were evaporated and the residue dissolved in 200 ml of methylene chloride. 600 ml of hexane were added to the solution with stirring at 30° and then another 600 ml of hexane at 0°. The suspension was filtered and the residue washed with hexane and then dried. 114.02 g (74%) of a 74.7:23.5:1.4:0.4 mixture of the (2S,3S):(2R,3S):(2R,3R):(2S,3R) isomers of 3-(1,3-dioxo-2,3-dihydro-1H-isoindol-2-yl)-2-hydroxy-4-phenylbutyronitrile were obtained, melting point 127.2°–130.5°, $[\alpha]_D^{20}$: −146.60° (1% in methylene chloride).

EXAMPLE 4
(V→VI)

A solution of 47.5 g of sodium pyrosulphite in 500 ml of water was added with stirring at room temperature to the solution containing 3-phenyl-2(S)-phthalimidopropan-1-al (Example 1). After 7.5 hours' stirring, the aqueous layer containing the addition product of pyrosulphite and the above aldehyde was washed with toluene. The toluene layers were extracted with water. A solution of 24.2 g of sodium cyanide in 200 ml of water were added to the water layers with stirring at room temperature. After 1 hour's stirring, the suspension was filtered and the residue washed with water until neutral. After drying, 112.03 g (73%) of a 67.2:32.8 mixture of the (2S,3S):(2R,3S) isomers of 3-(1,3-dioxo-2,3-dihydro-1H-isoindol-2-yl)-2-hydroxy-4-phenylbutyronitrile, melting point 131°–133°, $[\alpha]_D^{20}$: −150.2° (1% in methylene chloride).

EXAMPLE 5
(VI→VIII via VII)

A suspension of 100 g of 3-(1,3-dioxo-2,3-dihydro-1H-isoindol-2-yl)-2-hydroxy-4-phenylbutyronitrile as a 73.6:26.4 mixture of the (2S,3S) and (2R,3S) isomers (Example 23) in 500 ml of 25% hydrochloric acid was refluxed for 17 hours, cooled to 0° and stirred for 1 hour at 0°. Once the precipitated phthalic acid (52 g, 96%) had been filtered out, the filtrate was adjusted at 25° to pH 7.5 with 40% sodium hydroxide solution and combined with 46.6 ml of ethyl chloroformate, the pH value being maintained between 7 and 8 with 40% sodium hydroxide solution. Once conversion was complete (approximately 1 hour), the solution was adjusted to pH 1 with 37% hydrochloric acid and extracted with ethyl acetate. The extracts were washed with water, dried over magnesium sulphate and filtered and the filtrate evaporated. The residue was crystallised from 400 ml of toluene and the crystallisate dried, wherein 52 g (60%) of a 99:1 mixture of the (2S,3S):(2R,3S) isomers of 3-ethoxycarbonylamino-2-hydroxy-4-phenylbutyric acid, melting point 138.4°–140.50°, were obtained.

IR(KBr): 3433 m and 3309 s (NH, OH), 2900–2400 w, br. (COOH), 1736 s and 1689 s (C=O).

$^1$H-NMR (d$_6$-DMSO): 12.6 (s, br., 1H, COOH) ; 7.30–7.00 (m, 6H, H—Ar., NH); 5.5 (s, br., 1H, OH); 4.10–3.60 (m, 4H, CH$_2$CH$_3$, CHN, CH—OH); 2.80–2.50 (m, 2H, CH$_2$—Ar.).

MS (EI): 222 (10, M—COOH).

EXAMPLE 6
(VIII→IX)

A suspension of 8.02 g of 3-ethoxycarbonylamino-2-hydroxy-4-phenylbutyric acid in 60 ml of water was combined at room temperature with 20 ml of 3N sodium hydroxide solution and stirred at room temperature for 8½ hours. The solution was adjusted to pH 7 with 3.8 ml of 25% hydrochloric acid, evaporated to 20 ml under reduced pressure and adjusted to pH 1 with 6 ml of 25% hydrochloric acid. The reaction mixture was then stirred at 0° for 2½ hours, filtered and washed with iced water, wherein 5.47 g (82%) of pure (4S,5S)-4-benzyl-2-oxo-oxazolidine-5-carboxylic acid, melting point 177°–179°, were obtained.

EXAMPLE 7
(IX→X)

A solution of 8.85 g of (4S,5S)-4-benzyl-2-oxo-oxazolidine-5-carboxylic acid in 45 ml of methanol and 0.5 ml of sulphuric acid is refluxed for 2 hours, evaporated to 15 ml and cooled to −15°. Once filtered out, the residue is dried, wherein the 4-benzyl-2-oxo-oxazolidine-5-carboxylic acid methyl ester is obtained as a 98:2 mixture of the (4S,5S) and (4S,5R) isomers, melting point 93°–94.5°.

EXAMPLE 8
(XX→XI)

150 g of the 98:2 mixture of the (4S,5S) and (4S,5R) isomers of 4-benzyl-2-oxo-oxazolidine-5-carboxylic acid methyl ester were added at 15°–20° over a period of 1.5 hours to a stirred solution of 20.8 g of sodium borohydride in 360 ml of ethanol and then stirred for a further 2 hours. The suspension was combined at 20° with 540 ml of water and the pH value adjusted to 7 with 165 ml of 3N hydrochloric acid. The suspension was stirred at room temperature for 2.5 hours, left to stand for 18 hours at 4° and then filtered. The residue was washed with water and dried and yielded 111.6 g (84%) of 99% (4S,5S)-4-benzyl-5-hydroxymethyl-oxazolidin-2-one, melting point 167.3°–168.9°, [α]$_D^{20}$: −79.4° (1% in methanol).

EXAMPLE 9
(XI→XII)

A solution of 4.7 ml of methanesulphonyl chloride in 10 ml of acetone were added at 250° to a suspension of 10.4 g of (4S,5S)-4-benzyl-5-hydroxymethyl-oxazolidin-2-one in 20 ml of acetone and 6.1 ml of N-methyl-morpholine and the suspension was stirred for 3 hours at 25°. A further 1.1 ml of N-methylmorpholine were added and stirring continued for 1 hour. The suspension was shaken with 80 ml of semi-saturated sodium bicarbonate solution and ethyl acetate and the separated aqueous phase extracted with ethyl acetate. The ethyl acetate extracts were washed with water, dried and filtered. The filtrate was evaporated and yielded 14.3 g (100%) of crude methanesulphonic acid (4S,5S)-4-benzyl-2-oxo-oxazolidin-5-yl methyl ester, TLC (SiO$_2$, ethyl acetate) R$_f$=0.4; MS (EI): 286 (M+H)$^+$.

EXAMPLE 10
(XI→XII)

In a similar manner to Example 9, 88.2 g (93%) of o-nitrobenzenesulphonic acid (4S,5S)-4-benzyl-2-oxo-oxazolidin-5-yl methyl ester, TLC (SiO$_2$, ethyl acetate: R$_f$=0.38; MS (EI): 393 (M+H)$^+$, were obtained from 50 g of (4S,5S)-4-benzyl-5-hydroxymethyl-oxazolidin-2-one and 80 g of o-nitrobenzenesulphonyl chloride.

EXAMPLE 11
(XI→XII)

5.6 ml of triethylamine were added at room temperature to a stirred suspension of 5.55 g of (4S,5S)-4-benzyl-5-hydroxymethyl-oxazolidin-2-one in 27 ml of acetone and 6.64 g of p-toluenesulphonyl chloride and the mixture stirred for 6.5 hours at room temperature. The suspension was combined with water, stirred at 10° and filtered and the residues washed with a (3:2) water/acetone solution and evaporated, yielding 9.09 g (94%) of 99% p-toluenesulphonic acid (4S,5S)-4-benzyl-2-oxo-oxazolidin-5-yl methyl ester, melting point 148.7°–150.3°, [α]$_D^{20}$: +3.0° (1% in acetone)

EXAMPLE 12
(XI→XII)

15.4 g of 4-nitrobenzenesulphonyl chloride were added in portions at room temperature to a stirred suspension of 12.0 g of (4S,5S)-4-benzyl-5-hydroxymethyl-oxazolidin-2-one in 35 ml of tetrahydrofuran and 7.66 ml of N-methylmorpholine and the mixture stirred for 4.5 hours. A further 0.77 ml of N-methylmorpholine were added to the suspension and the mixture stirred for 4.5 hours at room temperature. The mixture was combined with 70 ml of a 2% sodium bicarbonate solution, stirred for 1.5 hours and filtered and the residue was washed with water and ethanol, wherein 21.4 g (94%) of 98.5% p-nitrobenzene-sulphonic acid (4S,5S)-4-benzyl-2-oxo-oxazolidin-5-yl methyl ester, melting point 148°–149.5°, [α$^-$]$_D^{20}$: +10.0° (1% in acetone) were obtained.

EXAMPLE 13

In a similar manner to Example 12, 65.5 g (91%) of p-bromobenzenesulphonic acid (4S,5S)-4-benzyl-2-oxo-oxazolidin-5-yl methyl ester, melting point 151.6°–153°, were obtained from 35 g of (4S,5S)-4-benzyl-5-hydroxymethyl-oxazolidin-2-one and 56.1 g of p-bromobenzenesulphonyl chloride.

EXAMPLE 14
(V→VI)

A solution of 11.16 g of 3-phenyl-2(S)-phthalimidopropan-1-al and 0.7 g of benzyltriethylammonium chloride in 70 ml of methylene chloride was combined with stirring at −10° with 6.2 ml of benzyl chloroformate. A solution of 3.10 g of sodium cyanide in 50 ml of water was then added dropwise. After 0.5 hours at −10°, the temperature was raised to 0°. The methylene chloride phase was washed with water and with saturated common salt solution. The aqueous phase was extracted with methylene chloride. The methylene chloride extracts were dried and filtered and the filtrate evaporated. The residue yielded 18.33 g of a 70:30 mixture of (2S,3S)- and (2R,3S)-3-(1,3-dioxo-1,3-dihydroisoindol-2-yl)-2-benzyloxycarbonyloxy-4-phenylbutyronitrile, MS (EI): 349 (6, M$^+$—C$_6$H$_5$CH$_2$), 288 (6, M$^+$—C$_6$H$_5$CH$_2$OCOOH), 91 (100, C$_6$H$_5$CH$_2$); IR (film): 2240 w (CN), 1763 s and 1717 s (C=O of imide and carbamate).

A suspension of 2 g of a 70:30 mixture of (2S,3S)- and (2R,3S)-3-(1,3-dioxo-1,3-dihydroisoindol-2-yl)-2-benzyloxycarbonyloxy- 4-phenylbutyronitrile and 0.15 g of palladium on carbon (10%) in 12 ml of ethanol and 2 ml of methylene chloride was hydrogenated for 2 hours at room temperature, then filtered and finally washed with methylene chloride and the filtrate evaporated. 1.35 g (97%) of a 72:27 mixture of (2S,3S)- and (2R,3S)-3-(1,3-dioxo-1,3-dihydro-1H-isoindol-2-yl)-2-hydroxy-4-phenylbutyronitrile, IR (KBr): 3450 m (OH), 2250 w (C≡N), 1775 m and 1712 s (C=O of imide) were obtained in this manner.

EXAMPLE 15
(XII→XIV)

A) A suspension of 24.69 g of p-nitrobenzenesulphonic acid (4S,5S)-4-benzyl-2-oxo-oxazolidin-5-yl methyl ester, 15.0 g of N-tert.-butyl-decahydro-(4aS,8aS)-isoquinoline-3(S)-carboxamide and 10.0 g of sodium carbonate in 76 ml of 4-methyl-2-pentanone were refluxed with stirring for 10 hours. The suspension was cooled to 80°, diluted with 176 ml of 4-methyl-2-pentanone and 54 ml of 3N hydrochloric acid, cooled to 40° and filtered. The residue was washed with water and 4-methyl-2-pentanone and yielded 35.1 g (88%) of (3S,4aS,8aS)-2-[(4S,5R)-4-benzyl-2-oxo-oxazolidin-5-yl methyl]-N-tert.-butyl-decahydro-isoquinoline-3-carboxamide-p-nitrobenzene-sulphonate, sulphonate, $[\alpha]_D^{20}=-31.2°$ (1% in dimethylformamide)

B) The same salt was obtained at a yield of 89% when triethylamine (2 mol equivalents) was used instead of sodium carbonate.

EXAMPLE 16

In a similar manner to Example 15B), 11.8 g (40%) of (3S,4aS,8aS)-2-[(4S,5R)-4-benzyl-2-oxo-oxazolidin-5-yl methyl]-N-tert.-butyl-decahydro-isoquinoline-3-carboxamide-p-toluenesulphonate, melting point 203°–205°, were obtained by reacting 14 g of methanesulphonic acid (4S,5S)-4-benzyl-2-oxo-oxazolidin-5-yl methyl ester with 11.7 g of N-tert.-butyl-decahydro-(4aS,8aS)-isoquinoline-3(S)-carboxamide after the addition of 1 mol equivalent of p-toluenesulphonic acid.

EXAMPLE 17

In a similar manner to Example 15B), 5.4 g (45%) of (3S,4aS,8aS)-2-[(4S,5R)-4-benzyl-2-oxo-oxazolidin-5-yl methyl]-N-tert.-butyl-decahydro-isoquinoline-3-carboxamide-p-toluenesulphonate, melting point 202°–204°, were obtained by reacting 7.2 g of p-toluenesulphonic acid (4S,5S)-4-benzyl-2-oxo-oxazolidin-5-yl methyl ester with 4.8 g of N-tert.-butyl-decahydro-(4aS,8aS)-isoquinoline-3(S)-carboxamide.

EXAMPLE 18

In a similar manner to Example 15B), 36.5 g (78%) of (3S,4aS,8aS)-2-[(4S,5R)-4-benzyl-2-oxo-oxazolidin-5-yl methyl]-N-tert.-butyl-decahydro-isoquinoline-3-carboxamide-p-bromophenylsulphonate, $[\alpha]_D^{20}=-29.9°$ (1% in dimethylformamide) were obtained by reacting 30 g of p-bromobenzenesulphonic acid (4S,5S)-4-benzyl-2-oxo-oxazolidin-5-yl methyl ester with 16.8 g of N-tert.-butyl-decahydro-(4aS,8aS)-isoquinoline-3(S)-carboxamide.

EXAMPLE 19

In a similar manner to Example 15B) 42 g (70%) of (3S, 4aS, 8aS)-2-[(4S, 5R)-4-benzyl-2-oxo-oxazolidin-5-yl methyl]-N-tert.-butyl-decahydro-isoquinoline-3-carboxamide-p-toluenesulphonate, $[\alpha]_D^{20}=-34.2°$ (1% in dimethylformamide) were obtained by reacting 39.2 g of 2-nitrobenzenesulphonic acid (4S,5S)-4-benzyl-2-oxo-oxazolidin-5-yl methyl ester with 23.8 g of N-tert.-butyl-decahydro-(4aS, 8aS)-isoquinoline-3(S)-carboxamide.

EXAMPLE 20
(XIV→I)

34.7 g of (3S,4aS,8aS)-2-[(4S,5R)-4-benzyl-2-oxo-oxazolidin-5-yl methyl]-N-tert.-butyl-decahydro-isoquinoline-3-carboxamide-p-nitrobenzenesulphonate were divided between 110 ml of ethyl acetate and 110 ml of saturated sodium bicarbonate. The aqueous layer was extracted with ethyl acetate and the ethyl acetate extracts washed with 110 ml of saturated sodium bicarbonate and with water. The organic extracts were evaporated and the residue diluted with 55 ml of ethanol and combined with stirring with a solution of 11.0 g of sodium hydroxide in 55 ml of water. The mixture was refluxed for 5 hours, diluted with 55 ml of water and cooled to room temperature. The suspension was filtered and the residue washed with water until the filtrate was neutral. The residue was evaporated and yielded 20.7 g (93%) 2-[3(S)-amino-2(R)-hydroxy-4-phenylbutyl]-N-tert.-butyl-decahydro-(4aS, 8aS)-isoquinoline-3(S)-carboxamide, melting point 175°–176°.

EXAMPLE 21
(VI→XV)

A) A solution of 100 g of 3-(1,3-dioxo-1,3-dihydroisoindol-2-yl)-2-hydroxy-4-phenylbutyronitrile (Example 3) in 450 ml of CH$_2$Cl$_2$ is added at 0° C. to a solution of 400 g of HCl in 980 ml of methanol. After 18 hours' stirring at 0° C., the suspension is filtered. The resultant residue containing imino ether HCl is added to a mixture of 600 ml of each of ethyl acetate and water. Once the solid has dissolved, the aqueous layer is extracted with ethyl acetate. The organic layers are washed with saturated NaHCO$_3$ solution and with water and are then dried. The suspension is filtered and the filtrate evaporated to yield 77.15 g (70%) of a 93:7 mixture of the (2S,3S):(2R,3S) isomers of 3-(1,3-dioxo-1,3-dihydroisoindol-2-yl)-2-hydroxy-4-phenylbutyric acid methyl ester, $[\alpha]_D^{20}$: −121.5° (1% in ethyl acetate).

B) 120 g of HCl are passed at 0° C. into a solution of 200 g of 3-(1,3-dioxo-1,3-dihydroisoindol-2-yl)-2-hydroxy-4-phenylbutyronitrile (Example 3) in 1200 ml of toluene and 106 ml of methanol and the mixture is stirred for 3 hours at 0° C. The suspension is combined with 1200 ml of water and 400 ml of methanol and stirred for 2 hours at 22° C. The aqueous layer is extracted with toluene. The organic layers are washed, dried, filtered and the filtrate evaporated to yield 221 g (100%) of a 75:25 mixture of the (2S,3S):(2R,3S) isomers of 3-(1,3-dioxo-1,3-dihydroisoindol-2-yl)-2-hydroxy-4-phenylbutyric acid methyl ester, $[\alpha]_D^{20}$: −133.1° (1% in ethyl acetate)

EXAMPLE 22
(XV→XVI)

A) A solution of 20 g of a 93:7 mixture of the (2S,3S):(2R,3S) isomers of 3-(1,3-dioxo-1,3-dihydroisoindol-2-yl)-2-hydroxy-4-phenylbutyric acid methyl ester (Example 21) in 20 ml of methanol is treated with stirring at 0° C. with a solution of 11.75 ml of an 18.7% solution of methylamine in methanol and stirred for 4 hours at 0° C.

44 ml of a 20% solution of HCl in methanol are added to the solution at 0° C. After 3 hours' stirring at 22° C., the suspension is filtered, the residue washed with methanol and the filtrate evaporated. The pH of the residue is adjusted to 4 at 0° C. with dilute ammonia solution. The aqueous layer is washed with ethyl acetate, the organic layer extracted with water and the pH of the combined water layers adjusted to 9.3 at 22° C. with ammonia solution. The aqueous layer is repeatedly extracted with ethyl acetate, the organic layers dried, filtered and the filtrate evaporated to 50 g. The remaining solution is treated with 3.4 ml of acetic acid and stirred at 0° C. The suspension is filtered and the residue washed with ethyl acetate After drying, 13.83 g (87%) of a 98:2 mixture of the (2S,3S) and (2R,3S) isomers of 3-amino-2-hydroxy-4-phenylbutyric acid methyl ester acetate, melting point 113°–114.5° C., $[\alpha]_D^{20}$: +15.3° (1% in methanol) are obtained.

B) In a similar manner to Example 22A), 28.4 g (66%) of a 92:8 mixture of the (2S,3S) and (2R,3S) isomers of 3-amino-2-hydroxy-4-phenylbutyric acid methyl ester acetate, melting point 109°–110° C., $[\alpha]_D^{20}$: +13.6° (1% in methanol) were obtained by reacting 54.6 g of a 75:25 mixture of the (2S,3S):(2R,3S) isomers of 3-(1,3-dioxo-1,3-dihydroisoindol-2-yl)-2-hydroxy-4-phenylbutyric acid methyl ester (Example 19B).

EXAMPLE 23

(III→VI via IV, V)

A suspension of 100 g of 3-phenyl-2(S)-phthalimido-propionic acid in 810 ml of toluene was combined with stirring at 22° C. with 0.34 ml of DMF and 45.1 g of oxalyl chloride. The mixture was stirred for 3 hours at 22° C. Argon was passed into the solution. The solution was then combined with 59 ml of 1,2-butylene oxide. The mixture was then degassed and treated with a suspension of 15.9 g of Pd/C in 100 ml of toluene. The suspension was hydrogenated for 16 hours with stirring, then degassed and the suspension filtered under argon.

The residue was washed with toluene. The filtrate was combined with stirring at 22° C. with a solution of 32.2 g of sodium pyrosulphite and 320 ml of water. After 7 hours, the mixture was combined with a solution of 13 g of NaCN in 130 ml of water. After 30 minutes, the aqueous layer was separated and extracted with toluene. The toluene layers were washed with water and the combined layers evaporated. The resultant suspension was diluted with hexane with stirring and then filtered. The residue was washed with hexane/toluene (10/1). 80.9 g (78%) of 3-(1,3-dioxo-2,3-dihydro-1H-isoindol-2-yl)-2-hydroxy-4-phenylbutyronitrile were obtained as a 73.6:26.4 mixture of the (2S,3S) and (2R,3S) isomers, melting point 128°–132° C., $[\alpha]_D^{20}$: –151.4° (1% in methylene chloride)

EXAMPLE 24

(VI→IX via VII, VIII)

A suspension of 300 g of 3-(1,3-dioxo-2,3-dihydro-1H-isoindol-2-yl)-2-hydroxy-4-phenylbutyronitrile as a 74:26 mixture of the (2S,3S) and (2R,3S) isomers (Example 2) in 1500 ml of 25% hydrochloric acid was refluxed for 17 hours, treated with activated carbon, cooled to 0° C. and stirred for 1 hour. Once the suspension had been filtered, the filtrate was adjusted at 0–20° C. to pH 8.5 with 40% sodium hydroxide solution and combined with 121 ml of methyl chloroformate, the pH value being maintained between 8 and 9 with 40% sodium hydroxide solution. After stirring at 0° C., the solution was adjusted to pH 12.9 at 22° C. with 98 ml of 40% sodium hydroxide. After 4 hours, the solution was adjusted to pH 3.5 with 160 ml of 25% hydrochloric acid and combined with a further 80 ml of 25% hydrochloric acid. The mixture was seeded with (4S,5S)-4-benzyl-2-oxo-oxazolidine- 5-carboxylic acid and adjusted to pH –0.4° with 25% hydrochloric acid. After 2 hours at –10° C., the suspension was filtered. 131.6 g (61%) of a 97.2:2.8 mixture of the (4S,5S):(4S,5R) isomers of 4-benzyl-2-oxo-oxazolidine-5-carboxylic acid, melting point 172°–174° C., $[\alpha]_D^{20}$: –106.2° (1% in methanol), were obtained.

EXAMPLE 25

(IX→XI via X)

A solution of 50 g of a 97.2:2.8 mixture of the (4S,5S):(4S,5R) isomers of 4-benzyl-2-oxo-oxazolidine-5-carboxylic acid in 300 ml of methanol was combined with 1 ml of sulphuric acid and refluxed for 3.5 hours. The solution was cooled to 0° C. and adjusted to pH 7 with a solution of 30% sodium methoxide in methanol. 10.26 g of sodium borohydride were added to the solution at 0°–3° C. After 1 hour's stirring at 0° C., the suspension is adjusted to pH 1 at 0°–20° C. with 25% hydrochloric acid. After the addition of water and stirring at –10° C., the suspension is filtered. 41.5 g (89%) of 99% (4S,5S)-4-benzyl-5-hydroxymethyl-oxazolidin-2-one, melting point 168°–171° C., $[\alpha]_D^{20}$: –79.1° (1% in methanol), were obtained.

EXAMPLE 26

(III→XVI via IV, V, VI, VI')

a) 295 g of phthaloyl-L-phenylalanine (obtained by reacting L-phenylalanine with phthalic anhydride in toluene with refluxing) is suspended in 2.4 l of toluene. 1 ml of DMF is added and 140 g of oxalyl chloride added dropwise. After 3 hours' stirring at room temperature, any hydrogen chloride still present is removed under a water-jet vacuum.

b) After the addition of 200 ml of 1,2-butylene oxide and 47 g of Pd on carbon (5%) in 200 ml of toluene, the mixture is hydrogenated at 20° C. and a hydrogen pressure of 5 bar until no further hydrogen is absorbed.

c) Once the catalyst has been filtered out, the reaction mixture is evaporated under a vacuum at 40° C. 250 ml of water and a solution of 49 g of NaCN in 200 ml of water are added dropwise at 15°–20° C. The pH value of the solution is maintained at 6.5–7.3 by adding concentrated hydrochloric acid. Stirring is continued for a further 5–7 hours. The aqueous phase is then separated, extracted with water and the toluene phases are diluted with methanol. Yield of cyanohydrin in solution: 85–90% (HPLC).

d) The solution is cooled to –5° C. with stirring and 184 g of (liquid) hydrogen chloride are introduced at a maximum of 0° C. After 6–8 hours, 1.5 l of a solution of methanol in water (1:2) are added. The temperature rises to 20° C. Once the precipitate has dissolved, the lower aqueous phase is separated and extracted with toluene. The toluene phases are extracted with water. The toluene phase is then concentrated under a vacuum at 40° C.

e) The concentrated solution is diluted with 350 ml of methanol and combined at 0° C. with 38.4 g of methylamine in 30 ml of methanol. After 3 hours' stirring, a solution of 164 g of hydrogen chloride in 850 ml of methanol is added in such a manner that the internal temperature does not exceed 20° C. The reaction is allowed to continue for 4–6 hours and the precipitate is then filtered out. The precipitate is washed with methanol and the filtrates combined. After vacuum concentration, the mixture is diluted with water and adjusted to a pH value of 3 with 50% NaOH at 0° C. The aqueous phase is extracted with ethyl acetate. The aqueous phase contains a 75:25 mixture of the (2S,3S) and (2R,3S) isomers of 3-amino-2-hydroxy-4-phenylbutyric acid methyl ester hydrochloride (yield 75–806%).

EXAMPLE 27
(XVI→VII)

80 ml of a solution of the 75:25 mixture of the (2S,3S) and (2R,3S) isomers of 3-amino-2-hydroxy-4-phenylbutyric acid methyl ester hydrochloride from Example 26e) in water were concentrated under a vacuum to 50 ml. 17.5 ml of aqueous 25% $NH_3$ solution were then added. After 6–8 hours' reaction time, the mixture was cooled to 0° C. and the precipitated solid filtered out. The filter cake was washed with ethanol and dried under a vacuum at 55° C. 2.1 g (30% relative to the starting phthaloyl-L-phenylalanine of Example 26) of 3-amino-2-hydroxy-4-phenylbutyric acid were obtained as a 98:2 mixture of the (2S,3S) and (2R,3S) isomers.

EXAMPLE 28
(XVI→VII)

134.7 g of a 92:8 mixture of the (2S,3S) and (2R,3S) isomers of 3-amino-2-hydroxy-4-phenylbutyric acid methyl ester acetate (Example 22B) in 250 ml of water were added dropwise to a solution of 50 g of NaOH in 350 ml of water at a temperature of 40° C. The pH value fell from an initial value of 13.25 to 12.7. The mixture was stirred for a further 1 hour at 40° C. and was then neutralised to pH 6.5 at room temperature with 66 ml of 32% HCl. The solution was concentrated under a vacuum and cooled to 0° C. The solid was removed by suction filtration and washed with ethanol. The product was then dried under a vacuum at 55° C. Yield: 90.4 g (92.6% of theoretical) of 3-amino-2-hydroxy-4-phenylbutyric acid as an 87.7:12.3 mixture of the (2S,3S) and (2R,3S) isomers.

EXAMPLE 29
(XVI→VIII→IX)

a) An aqueous solution of a 75:25 mixture of the (2S,3S) and (2R,3S) isomers of 3-amino-2-hydroxy-4-phenylbutyric acid methyl ester hydrochloride (Example 26) was adjusted to pH 13 with sodium hydroxide solution. The pH value was maintained at pH 13 until it remained constant. A pH value of 9.5–10.5 was then established with concentrated HCl and the mixture cooled to 5° C. 200 ml of toluene were added and the mixture reacted with 123.2 g of ethyl chloroformate at 5°–10° C. while maintaining a constant pH (NaOH). On completion of the reaction, 100 ml of isopropyl acetate were added. The organic phase was separated and the isopropyl acetate removed from the aqueous phase by evaporation under a vacuum at 50° C. The mixture was acidified to pH 2 with concentrated HCl and extraction performed with isopropyl acetate. The organic phases were concentrated. The mixture was then combined with cyclohexane. The precipitate was removed by suction filtration and washed with a little cyclohexane/isopropyl acetate (1:1). The product was then dried in air. Yield: 45 g=18% of theoretical (relative to phthaloyl-L-phenylalanine) of >99:1 mixture of the (2S,3S):(2R,3S) isomers of 3-ethoxycarbonylamino-2-hydroxy-4-phenylbutyric acid.

b) The mother liquor was evaporated under a vacuum at 50° C., the oily residue was suspended in water and adjusted to pH 14 with concentrated NaOH. Stirring was continued for 6 hours at room temperature. A pH of 1 was then established with concentrated HCl and the mixture extracted with ethyl acetate. The ethyl acetate phase was evaporated and precipitated with methyl tert.-butyl ether. The precipitate was removed by suction filtration and dried. Yield: 36 g=16.3° of theoretical (relative the phthaloyl-L-phenylalanine) of a 98:2 mixture of the (4S,5S):(4S,5R) isomers of 4-benzyl-2-oxo-oxazolidine-5-carboxylic acid.

EXAMPLE 30
(XVI→XVII)

A) 134.7 g of a 92:8 mixture of the (2S,3S) and (2R,3S) isomers of 3-amino-2-hydroxy-4-phenylbutyric acid methyl ester acetate (Example 22B) were dissolved in 500 ml of water and cooled to 0° C. A pH value of 9.5 was established with 20 g of NaOH (in 60 ml of water). 56 g of ethyl chloroformate were added dropwise with stirring at 0°–5° C. within 2 hours, the pH value being maintained between 9 and 9.5 by the simultaneous addition of 30 g of NaOH (in 90 ml of water). Once the addition of ethyl chloroformate was complete, stirring was continued for 1 hour at 0° C., the pH value being maintained at 9.5. The solid was filtered out and washed with water and then dried. Yield: 119.4 g (84.9% of theoretical) of a 98:2 mixture of the (2S,3S) and (2R,3S) isomers of 3-ethoxycarbonylamino-2-hydroxy-4-phenylbutyric acid methyl ester.

B) 300 ml of toluene were added to an aqueous solution of a 75:25 mixture of the (2S,3S) and (2R,3S) isomers of 3-amino-2-hydroxy-4-phenylbutyric acid methyl ester hydrochloride (Example 26) and the mixture cooled to 0° C. A pH value of 9.5 was then established with 50% sodium hydroxide solution with stirring. 204.6 g of benzyl chloroformate were then added dropwise at 0°–5° C. while maintaining a constant pH by the simultaneous addition of 50% sodium hydroxide solution. Once addition was complete, the mixture was stirred until a constant pH was established, 300 ml of petroleum ether were added and the precipitate washed with methyl tert.-butyl ether. The product was then dried under a vacuum at 55° C. Yield: 181.4 g (52.8% of theoretical) of a 10:1 mixture of the (2S,3S:2R,3S)[sic] isomers of 3-benzyloxycarbonylamino-2-hydroxy-4-phenylbutyric acid methyl ester.

EXAMPLE 31
(XVII→IX)

12 g of 500 sodium hydroxide solution are added to a solution of 42.2 g of a 10:1 mixture of the (2S,3S):(2R,3S) isomers of 3-ethoxycarbonylamino-2-hydroxy-4-phenylbutyric acid methyl ester in 150 ml of methanol. Stirring is continued for 15 minutes at 22° C. 16.2 g of sodium methylate are then added and stirring continued for a further 15 minutes with refluxing. 130 ml of methanol are removed by distillation with application of a vacuum at a maximum of 30° C. The residue is combined with water and stirred for 1 hour at 22° C. The mixture is then acidified to pH 1 with concentrated HCl and extracted with ethyl acetate. The ethyl acetate phase is evaporated under a vacuum at a maximum of 35° C. and combined with 150 ml of toluene or methyl tert.-butyl ether with stirring. After 2 hours' stirring, the precipitated solid is removed by suction filtration, washed with iced water and dried under a vacuum at 50° C. Yield: 26.6 g (80.1%) of 4-benzyl-2-oxo-oxazolidine-5-carboxylic acid as a mixture of the (4S,5S):(4S,5R) isomers (96:4 in toluene, 98:2 in methyl tert.-butyl ether).

EXAMPLE 32
(XVII→IX)

24 g of 50% sodium hydroxide solution are added to a solution of 42.2 g of a 10:1 mixture of the (2S,3S):(2R,3S) isomers of 2-ethoxycarbonylamino-2-hydroxy-4-phenylbutyric acid methyl ester in 150 ml of water and the mixture is stirred for 3–4 hours at 30°–35° C. The mixture is then acidified to pH 1 with concentrated HCl and extracted with ethyl acetate. The ethyl acetate phase is concentrated under a vacuum at a maximum of 35° C. and combined with 150 ml of toluene or methyl tert.-butyl ether with stirring.

After 2 hours' stirring, the precipitated solid is removed by suction filtration, washed with iced water and dried under a vacuum at 50° C. Yield: 27.3 g (82.2%) of 4-benzyl-2-oxo-oxazolidine-5-carboxylic acid as a mixture of the (4S,5S):(4S,5R) isomers (96:4 in toluene, 98:2 in methyl tert.-butyl ether).

EXAMPLE 33
(IX→XI)

a) 1.2 ml of (95–97%) sulphuric acid are added to a solution of 22.1 g of a 97.2:2.8 mixture of the (4S,5S):(4S,5R) isomers of 4-benzyl-2-oxo-oxazolidine-5-carboxylic acid (Example 24) in 120 ml of ethanol and the mixture is refluxed for 2 hours. The solution is then concentrated by the removal of 90 ml of ethanol by distillation.

b) The solution from a) is added dropwise at a maximum of 25° C. to a suspension of 5.3 g of sodium borohydride in 40 ml of ethanol. Once addition is complete, stirring is continued for 2–3 hours. Water is added to the white suspension and a pH of 7 is established with concentrated HCl. Stirring is continued first for 2 hours at 22° C. and then for a further 2 hours at 0° C. The solid is filtered out and washed with iced water. The product is then dried under a vacuum at 45° C. Yield: 18.68 g (90.1%) of a 98:2 mixture of the (4S,5S)(4S,5R) isomers of 4-benzyl-5-hydroxymethyl-oxazolidin-2-one.

EXAMPLE 34
(III→IX, via IV, V, VI, VII, VIII)

0.4 ml of dimethylformamide were added to a stirred suspension of 118.1 g of phthaloyl-L-phenylalanine in 720 ml of toluene and 37.7 ml of oxalyl chloride were added dropwise within 30 minutes. Once evolution of gas was complete, stirring was continued for 1 hour at room temperature and the mixture was then concentrated under a vacuum for 20 minutes under a vacuum[sic]. 95 ml of 1,2-epoxybutane were then added and the mixture stirred for 20 minutes at room temperature. 18.8 g of palladium on carbon (5%) were added and the mixture hydrogenated at a hydrogen pressure of 4 bar above atmospheric until hydrogen absorption ceased. The catalyst was filtered out and the residue washed with 70 ml of toluene, wherein a toluene solution of 3-phenyl-2(S)-phthalimidopropan-1-al was obtained.

This solution was combined with 100 ml of water and a solution of 20.7 g of NaCN in 93 ml of water was then added dropwise within an hour at 20°–25° C. with stirring. The pH value was maintained between 6 and 7.2 by the simultaneous dropwise addition of semi-concentrated HCl. Once addition was complete, stirring was continued for 10 hours at room temperature, the phases separated, wherein the aqueous phase was re-extracted with 100 ml of toluene and the combined toluene phases were washed with 100 ml of water at pH 3. Once the phases had been separated, a 74.5:25.5 mixture of the (2S,3S):(2R,3S) isomers of 3-(1,3-dioxo-2,3-dihydro-1H-isoindol-2-yl)-2-hydroxy-4-phenylbutyronitrile in a toluene solution was obtained.

After the addition of 100 ml of 21% aqueous HCl, the toluene was removed by azeotropic distillation, wherein the aqueous distillate was returned to the bottoms. Once the toluene had been distilled off, a further 415 ml of 21% aqueous HCl were added and the mixture refluxed for 16 hours. 463 g of aqueous HCl were then distilled off and the bottoms diluted with 165 ml of water. After cooling the mixture to 10° C., the solid was filtered out and washed twice with 32 ml portions of water.

70% of the aqueous filtrates (284.4 g) (they contain the 3-amino-2-hydroxy-4-phenylbutyric acid) were then extracted with 70 ml of isobutyl methyl ketone and the aqueous product phase was then diluted with 141 ml of water. Once 27 ml of 40% NaOH had been added at 20°–25° C., the temperature was reduced to <5° C. and 35 ml of methyl chloroformate were added dropwise. During this addition, the pH value was maintained in the range from 8–9 by the simultaneous addition of 57 ml of 40% NaOH. After a further 30 minutes' reaction, the solution was combined with 40.4 ml of 40% NaOH, wherein a pH value of 13.3 was obtained. After one hour, a pH value of 3.3 was established with 61 ml of aqueous 37% HCl and the aqueous phase was extracted with 70 ml of isobutyl methyl ketone.

The temperature was then raised to 60° C. and a further 42.6 ml of 37% HCl were added. On cooling to 0° C., a white crystalline precipitate formed which was filtered out after one hour's stirring at 0° C. and was washed twice with 100 ml of iced water.

The moist product was suspended in 230 ml of methyl tert.-butyl ether and dewatered azeotropically at standard pressure. The temperature was then reduced to 0° C., the product filtered out, washed twice with 20 ml of methyl tert.-butyl ether and dried. Yield: 27.72 g (45% of theoretical relative to introduced phthaloyl-L-phenylalanine) of 4-benzyl-2-oxo-oxazolidine-5-carboxylic acid. 4S,5S:4S,5R diastereomer ratio=96.3:3.7.

We claim:

1. Process for the production of 2-[3-(S)-amino-2(R)-hydroxy-4-phenylbutyl]-N-tert.-butyl-decahydro-(4aS,8aS)-isoquinoline-3(S)-carboxamide of the formula

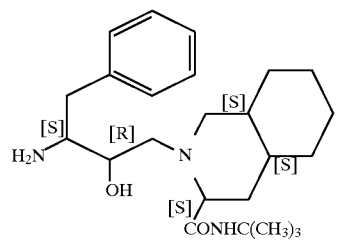

I characterised in that a) L-phenylalanine of the formula

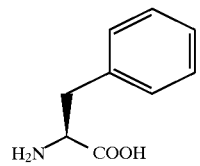

II is reacted with phthalic anhydride, b) the resultant 3-phenyl-2(S)-phthalimidopropionic acid of the formula

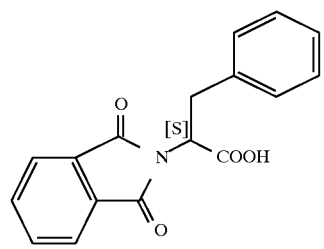

III is converted into the corresponding acid chloride, c) the resultant 3-phenyl-2(S)-phthalimidopropionic acid chloride of the formula

IV

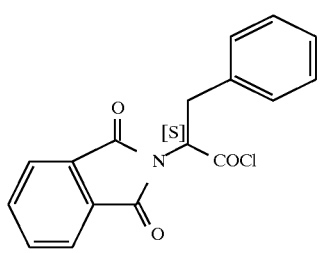

is reduced, d) the resultant 3-phenyl-2(S)-phthalimidopropan-1-al of the formula

V

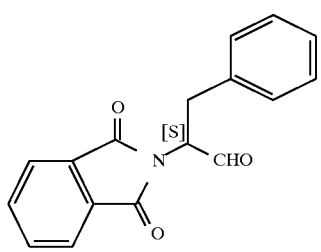

is transformed into the 1-cyano-3-phenyl-2(S)-phthalimidopropan-1-ol of the formula

VI

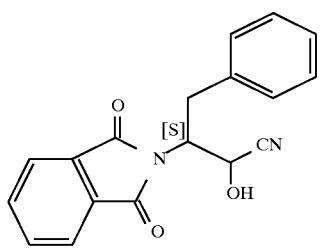

e) the resultant nitrile of the formula VI is hydrolysed,
f) the unisolated 3(S)-amino-2-hydroxy-4-phenylbutyric acid formed of the formula

VII

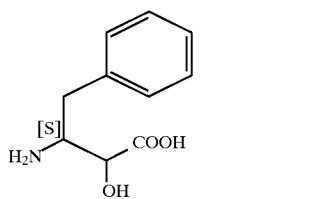

is reacted with a low alkyl ester or the phenyl or benzyl ester of chloroformic acid, g) a resultant 3(S)-[low alkoxycarbonylamino-, phenyloxycarbonylamino- or benzyloxycarbonxylamino]-2-hydroxy-4-phenylbutyric acid of the general formula

VIII

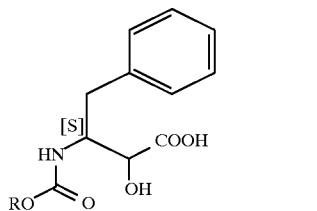

in which R means low alkyl, phenyl or benzyl, is cyclised, h) the resultant crystallized (4S,5S)-4-benzyl-2-oxo-oxazolidine-5-carboxylic acid of the formula

IX

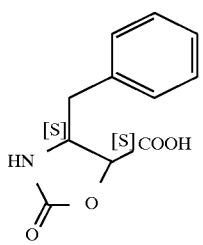

is esterified with a low alkanol, i) the resultant (4S,5S)-4-benzyl-2-oxo-oxazolidine-5-carboxylic acid low alkyl ester of the general formula

X

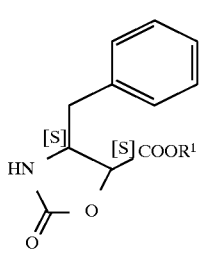

in which $R^1$ means low alkyl, is reduced j) the resultant (4S,5S)-4-benzyl-5-hydroxymethyl-oxazolidin-2-one of the formula

XI

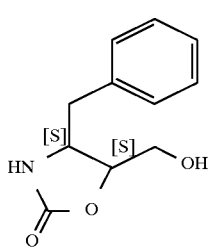

is reacted in the presence of a base with a sulphonic acid chloride of the general formula

$R^2$—$SO_2Cl$ in which $R^2$ means low alkyl, phenyl or phenyl mono- or disubstituted by halogen, low alkyl or nitro, k) a resultant sulphonic acid ester of the general formula

XII

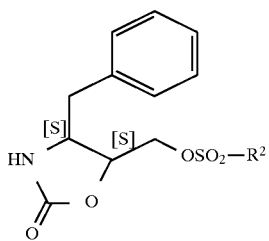

in which $R^2$ has the above-stated meaning, is reacted in the presence of a base with N-tert.-butyl-decahydro-(4aS,8aS)-isoquinoline-3(S)-carboxamide of the formula

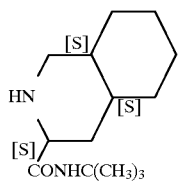
and
l) the resultant 2-[(4S,5R)-4-benzyl-2-oxo-oxazolidin-5-yl methyl]-N-tert.-butyl-decahydro-(4aS,8aS)-isoquinoline-3(S)-carboxamide of the formula
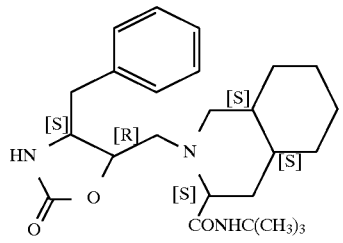
is treated with a base.
\* \* \* \* \*